United States Patent [19]

Mori

[11] Patent Number: 5,466,242

[45] Date of Patent: Nov. 14, 1995

[54] STENT FOR BILIARY, URINARY OR VASCULAR SYSTEM

[76] Inventor: Katsushi Mori, 3-1-810, Nishimidorigaoka 1-chome, Toyonaka-shi, Osaka, Japan

[21] Appl. No.: 190,303

[22] Filed: Feb. 2, 1994

[51] Int. Cl.[6] ................................................. A61F 2/06
[52] U.S. Cl. ................................................. 606/198; 623/1
[58] Field of Search ................................... 606/198, 200, 606/191; 623/1, 12

[56] References Cited

U.S. PATENT DOCUMENTS

| 4,503,569 | 3/1985 | Dotter | 3/1.4 |
|---|---|---|---|
| 4,665,908 | 5/1987 | Jervis | 128/92 YN |
| 4,795,458 | 1/1989 | Regan | 623/12 X |
| 5,037,427 | 8/1991 | Harada et al. | 606/194 |
| 5,067,957 | 11/1991 | Jervis | 606/108 |
| 5,201,901 | 4/1993 | Harada et al. | 606/198 |
| 5,231,989 | 8/1993 | Middleman et al. | 128/657 |
| 5,242,451 | 9/1993 | Harada et al. | 606/198 X |

Primary Examiner—Stephen C. Pellegrino
Assistant Examiner—Nancy Mulcare
Attorney, Agent, or Firm—Koda and Androlia

[57] ABSTRACT

A stent is made of shape memory alloy which has an Austenite finished temperature ranging from 41° C. to 43° C. The stent is capable of adopting a first configuration at a temperature below the Af and a second expanded configuration at or above the Af. In the first configuration, the stent comprises a proximal cylindrical portion, a distal cylindrical portion. The two portion are connected with an interspace therebetween. At the Af temperature the stent is reoriented, and at and above the Af temperature the proximal portion flares into a funnel conical shape expanding in maximum diameter and decreasing in diameter toward the distal portion. The distal cylindrical portion also expands in diameter, and the two portions directly connect with each other without the interspace. A method of placing the stent in position comprises inserting the stent in the first configuration into a system and subsequently raising the temperature of the stent to or above its Af temperature so that the stent assumes the second expanded configuration.

9 Claims, 8 Drawing Sheets

STENT FOR BILIARY, URINARY OR VASCULAR SYSTEM

BACKGROUND OF THE INVENTION

This invention relates to a stent for a biliary, urinary or vascular system, in particular a stent of shape memory alloy (SMA) to be placed in a pathologic stricture portion of the biliary, urinary or vascular system in the human body.

Urethral stents made of shape memory alloy have been developed and tested in small clinical trials. However such prior art stents have failed to provide a useful, practical treatment of prostatic obstruction.

Figure 9:
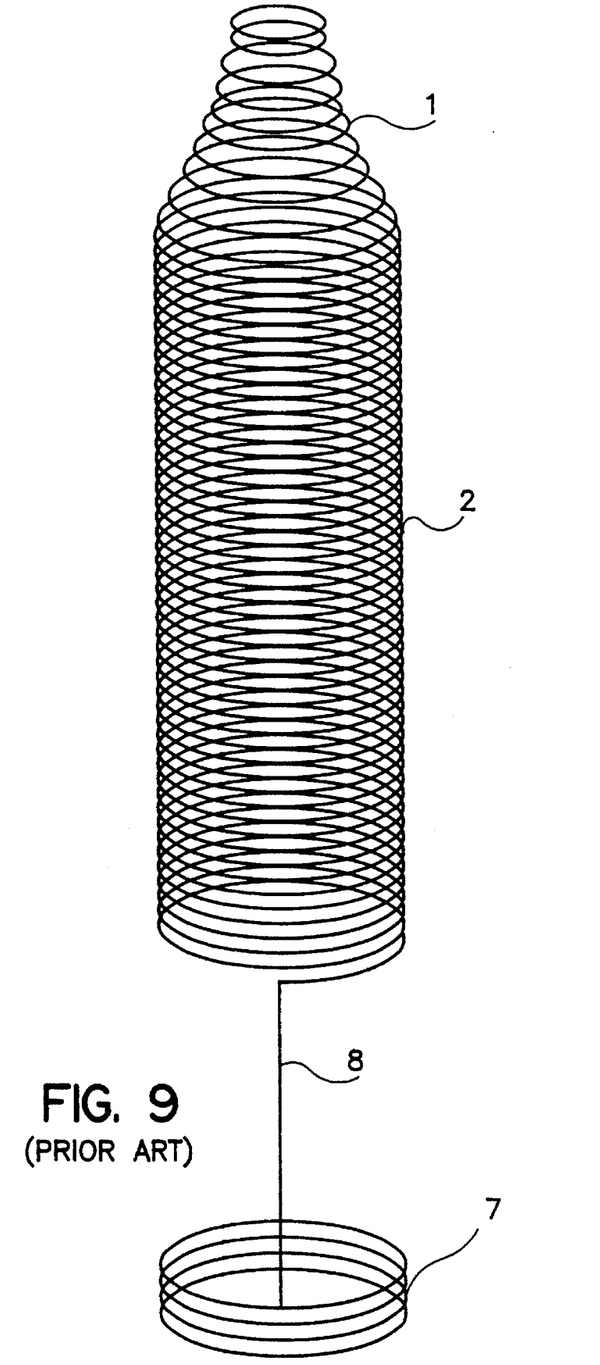
FIG. 9 is a perspective view of a conventional urethral stent.

An example of prior art stents is shown in FIG. 9, which comprises a spiral coil 2 with a proximal tapering end 1 and a distal hinge 7 for removal. In this context, an end of a stent which is to extend furthest into a patient's body is referred to as a "proximal" end, while the other end as a "distal" end. Another type of stent, which is not illustrated, is a cross woven cylindrical stent of, for example, 12 mm in diameter.

Such prior art stents have Austenite finished temperatures (Af temperatures) of about 48° C. or 36° C., respectively. Thus, the stents transform in shape at their respective Af temperatures.

An SMA stent having an Af temperature of 48° C. must be specially designed so that it does not burn the mucosa of the human body. In fact, the mucosa of the human body will be burned at temperatures of about 43° C. or above.

Another SMA stent having an Af temperature of 36° C. is more sensitive to temperature fluctuations and liable to change its shape inadvertently. For example, it could change its shape during transportation or storage because an ambient temperature in package or box is easy to be heated up to about 36° C., or perhaps in a doctor's or nurse's hand due to the human body temperature.

Furthermore, mesh stents require the assistance of an endoscope or other special accessory tool under ultrasonic or fluoroscopic control for accurate positioning and removal.

A stent may have to be removed for a variety of reasons, such as for example, once it has performed its function and is no longer necessary, or perhaps if it becomes encrusted, or if it migrates from its desired location such as into a bladder cavity. Thus, it can be very time consuming to use such stents. Also, they may occasionally traumatizes a uretra, a blood vessel or a bile duct, which may lead to bleeding or intolerable pain for patients.

SUMMARY OF THE INVENTION

It is a primary object of the present invention to provide a stent with which the aforementioned problems associated with prior art stents are alleviated.

It is an object of the present invention to provide a stent which may be used in a less invasive manner requiring no sedation in treatment of infravesical obstruction or the like.

It is another object of the present invention to provide a stent which is readily locatable in a desired position and removable from a patient simply on an out-patient basis.

In order to achieve the objects, a stent of the present invention is made of shape memory alloy which has an Austenite finished temperature (referred hereinafter to as Af) ranging from 41° C. to 43° C. The stent has a first configuration at a temperature below the Af and a second expanded configuration at or above the Af.

Thus, in the present invention, the shape memory alloy forming the stent has an Af temperature of from 41° C. to 43° C. so that the mucosa of a patient is net burned when the stent is used and the stent is less likely to transform in shape inadvertently.

The stent of the present invention preferably comprises, in its first configuration below the Af temperature, a proximal cylindrical portion, a distal cylindrical portion, and the two portions are connected with an interspace therebetween. However, at the Af temperature, the stent is reoriented to adopt a second, expanded configuration.

Thus, at and above the Af temperature, the proximal portion flares into a funnel shape which increases in diameter in the direction away from the distal portion. The distal cylindrical portion also expands in diameter, and the two portions directly connect with each other without the interspace.

The present invention also provide a method of locating a stent made of shape memory alloy having an Af temperature ranging from 41° C. to 43° C. in a desired position in a biliary, urinary or vascular system. The method comprises inserting a stent in a first configuration into such a system and subsequently raising the temperature of the stent to or above its Af temperature so that the stent assumes a second configuration.

Particularly the method involves the use of a stent which has, in its first configuration, a proximal cylindrical portion, a distal cylindrical portion and an interspace therebetween. The stent is located around an inflatable container or catheter and the catheter having the stent is inserted into a biliary or urinary tract or a blood vessel in a way that the proximal portion and the interspace portion pass through over a stricture part of the tract/vessel. 2 to 5 ml. of fluid such as water is infused into the catheter, causing the bag portion of the catheter to bulge or expand. The catheter with the stent located thereon is then pulled until the bulged bag portion abuts against the narrowing wall for an accurate positioning. The catheter is deflated and subsequently a flush of fluid such as saline at the Af temperature or above is fed into the catheter to reorient the stent to its expanded shade. And then the catheter is then withdrawn from the expanded stent for completion of the stent placement, thereby the stent being left in situ.

The stent of the present invention is constructed as above, when the stent is in an expanded configuration at and above the Af temperature, the neck portion of the funnel conical portion fits within a narrowing interior end portion of the stricture parts so that the stent is located firmly in position. The placement of the stent is readily completed with removal of the catheter from the stent because the stent is expanded in diameter.

DESCRIPTION OF THE PREFERRED EMBODIMENTS

The present invention is described in detail below with reference to the accompanying drawings.

A urethral stent according to the present invention is capable of adopting different configurations depending upon the temperature. In one embodiment, a stent is made of titanium and nickel, so called Shape Memory Alloy (SMA). The transforming temperature of this SMA ranges from 41° C. to 43° C., in this text referred to as Af (Austenite finished).

Figure 1:
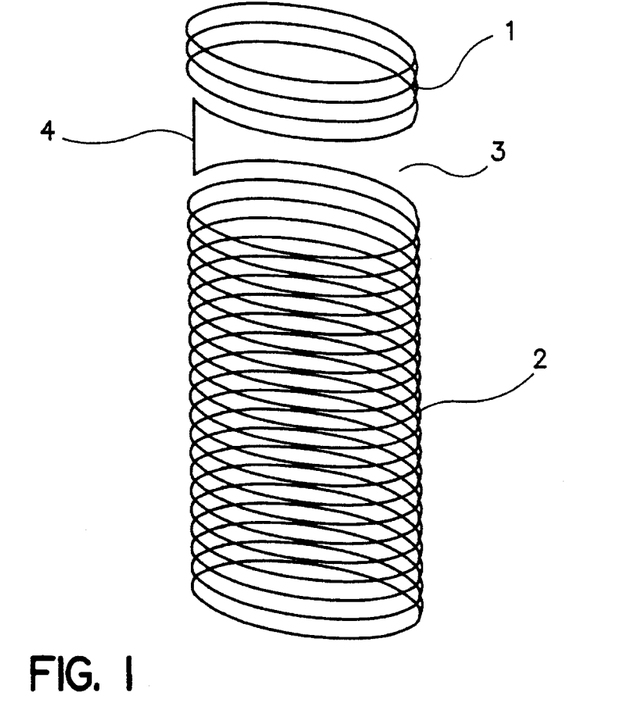
FIG. 1 is a perspective view showing a cold phase (Martensitic phase) configuration of an SMA urethral stent of the present invention.

As shown in FIG. 1, at an ambient temperature below Af, the configuration of the SMA stent is substantially cylindrical and includes a proximal coil portion 1, a distal coil portion and a straight wire portion 4. In this state both the coil portions 1, 2 are tightly coiled and the length of the proximal coil portion 1 is short, while that of the distal coil portion 2 is relatively long. There is an interspace 3 between the two coil portions 1, 2 and the straight wire portion 4 connects the two coil portions 1, 2. The cylindrical coil portion may be ellipsoidal or circular in cross section.

Figure 2:
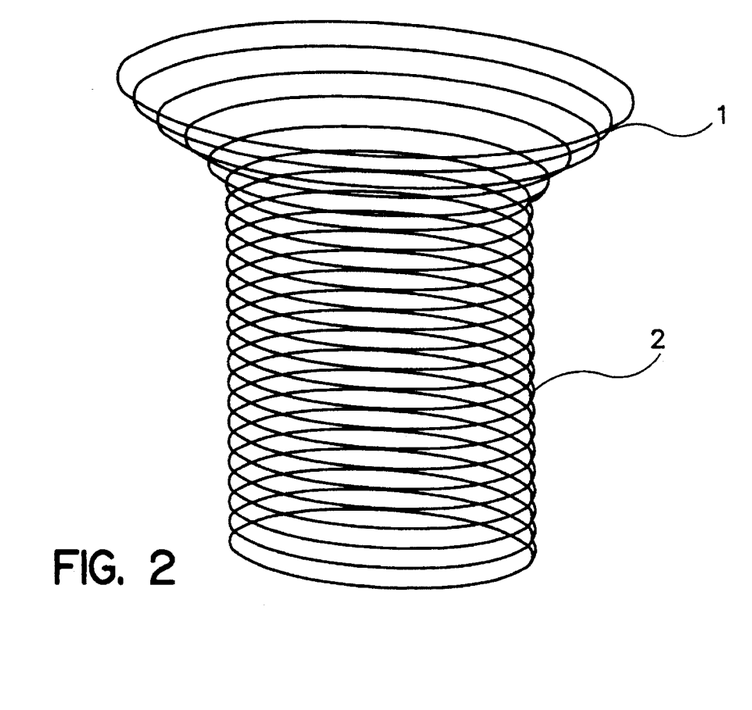
FIG. 2 is a perspective view of a hot phase (Af) configuration of the SMA urethral stent of FIG. 1.

At an ambient temperature of and above the Af, as shown in FIG. 2, the SMA stent is reoriented to a wholly expanded coil with an anchoring conical portion 1 tapering in diameter and a long circular cylindrical portion 2 and the shape of the wire portion 4 is absorbed into the shape combined the portions 1, 2. Thus, there is no interspace 3 between the two portions 1, 2.

In the SMA urethral stent, at the Martensitic state or below the Af temperature, the proximal coil portion 1 is, for example, about 5 mm both in length and diameter, the distal coil portion 2 is about 45 mm in length and about 5 mm in diameter, the distance of the interspace 3 is about 10 mm. At the Af temperatures each portion of the SMA urethral stent respectively expands. In this embodiment, the proximal coil portion 1 becomes 3 mm in length and the flared end thereof measures 15 mm in diameter. The distal portion 2 becomes 30 mm in length and 10 mm in diameter. The diameter of the entire length of the stent is to be kept at 10 mm or more to secure the urinary bladder empty without any encrustation or impacts so that the stent may be retained for a longer period.

The present invention is not limitative to a coiled stent, but also may be applied to a mesh stent or the like. Also other shape memory alleys with boundary temperature ranging from 41° C. to 43° C., such as of copper and zinc, may be utilized.

A method of placement and removal of the SMA urethral stent is described below.

Figure 3:
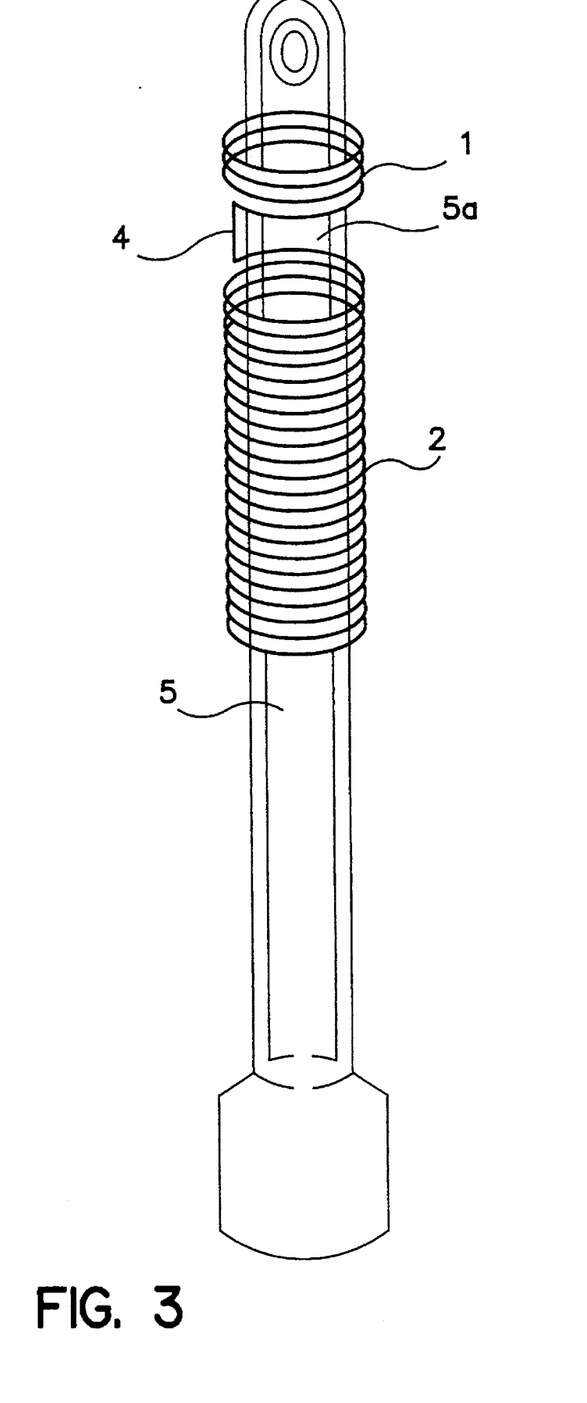
FIG. 3 is an explanatory diagram of the SMA stent fitted around a catheter in preparation.

In preparation, as shown in FIG. 3, a tightly coiled SMA urethral stent is fitted around a Foley catheter 5 in a way that the proximal portion 1 of the stent is at the insertion tip side of the catheter 5 and an interspace 3 of the SMA stent is at a bag portion or balloon portion 5a of the catheter 5.

Figure 4:
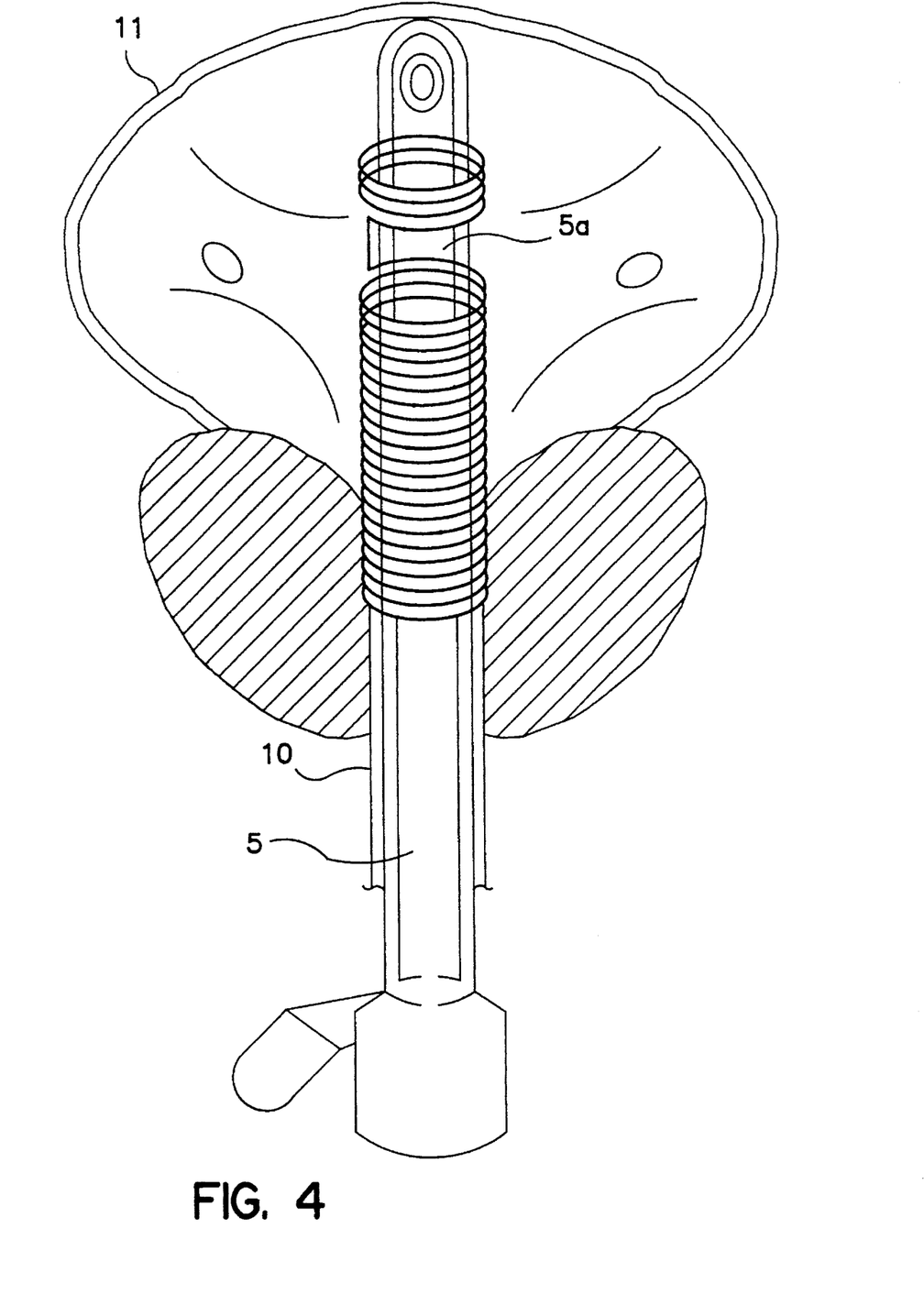
FIG. 4 is an explanatory diagram showing a Foley catheter with a spiral SMA urethral stent of the present invention which is introduced into and then passed over a narrow urethra into a bladder cavity.
Figure 5:
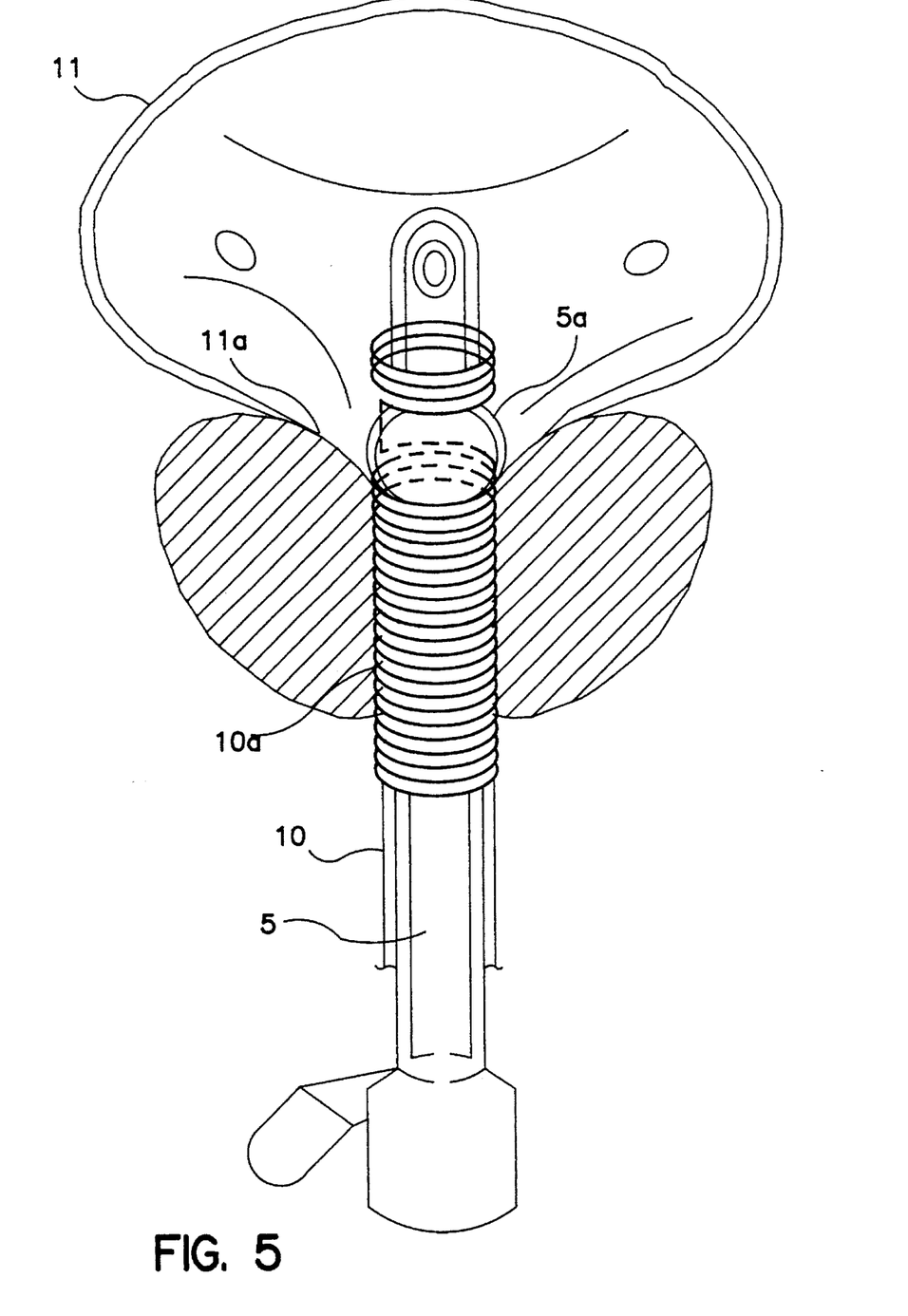
FIG. 5 is an explanatory diagram showing how the SMA urethral stent of FIG. 4 is accurately positioned by inflating a bag.

To place the stent, firstly, the Foley catheter 5 with the stent prepared as above is introduced into the urethra 10 and passed into the bladder cavity 11 in such a way that the proximal portion 1 and the interspace portion 3 corresponding to the bag portion 5a get into the bladder cavity 11, as shown in FIG. 4. By infusing water into the catheter 5, the bag portion 5a is bulged out from the interspace 3 of the SMA stent. Accurate positioning of the SMA stent may be achieved here by pulling the stent outwardly until the bulged bag portion 5a comes to abut against the bladder cervical region 11a, as shown in FIG. 5.

Figure 6:
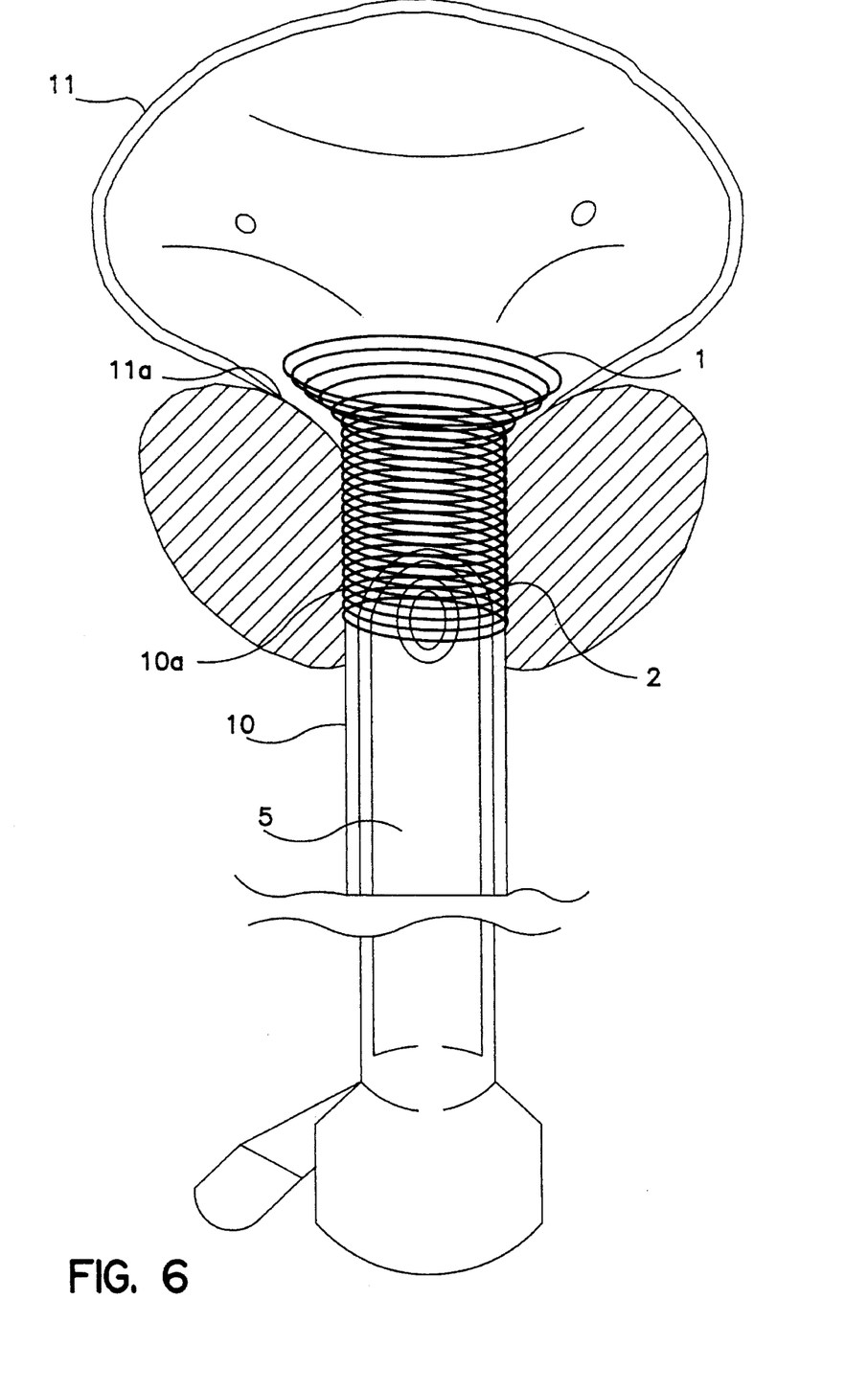
FIG. 6 is an explanatory diagram showing the SMA urethral stent of FIG. 5 being left in situ at a desired position in the urethra at the prostate.

Subsequently the catheter 5 is deflated. After that, a flush of saline at a temperature of 41° C. or above is fed into the catheter 5 to warm the SMA stent above the Af temperature. The stent, which changes its shape due to thermally induced expansion as shown in FIG. 6, is positioned at thee narrowing segment 11a, 10a of the urethra 10. Thus, the proximal portion 1 is located at the bladder cervical region 11a and the distal portion 2 is located in the urethra 10a at the prostate. At this stage, removal of the Foley catheter 5 leaves the stent in situ and located in the desired position. Since the stent is in the expanded state, the catheter 5 is easily removed from the stent.

When the stent is no longer necessary or needs to be renewed, removal of the SMA stent is to be performed as follows.

Figure 7:
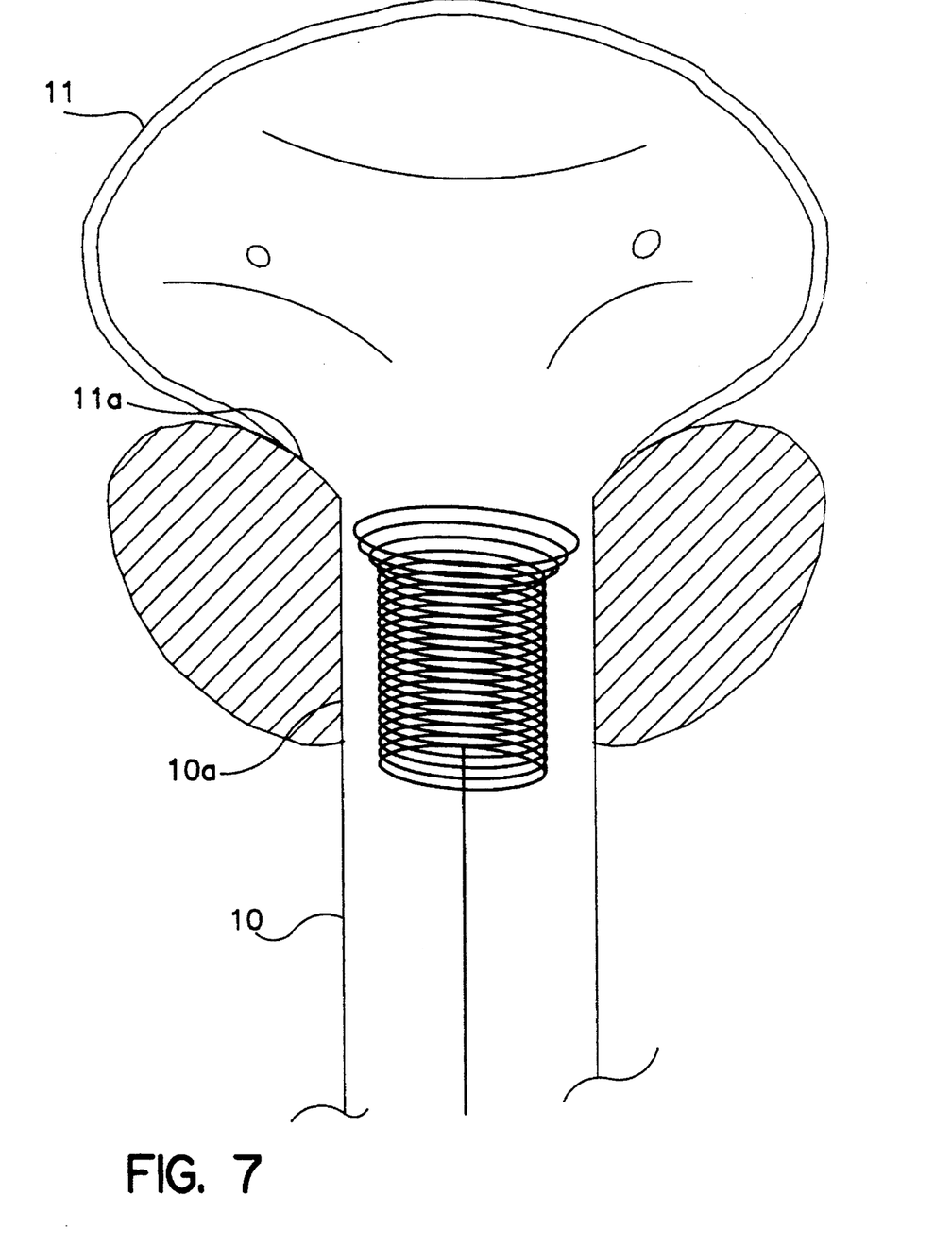
FIG. 7 is an explanatory diagram showing how the SMA urethral stent of FIG. 4 is removed by cooling.

A Foley catheter is introduced into the retaining SMA stent. A flush of cold saline below Martensitic transforming temperature of 25° C. into the catheter cools the stent, which actuates super-elastic transformation of the stent and causes the stent to be a fine cylinder shape (as shown in FIG. 7) or a straightened wire, so that the stent may be pulled out from a body orifice. It is preferable that the stent has a string at the end of the distal portion 2, so that the stent is readily to be pulled out by hand.

An SMA stent of the present invention is not limitative to a urethral stent but may be used also for the biliary or vascular system. Stents for biliary or vascular system are smaller in diameter, but the diameter of the entire passage should measure about 1 mm or more to ensure a blood or bile flow without an encrustation or impact, thereby the stent being retained for a longer period.

For placement of the SMA stent for biliary or vascular system, a set of guide and catheter is necessary. In preparation, an SMA stent is applied around the catheter 5 in the same way for the urethral stent.

Figure 8:
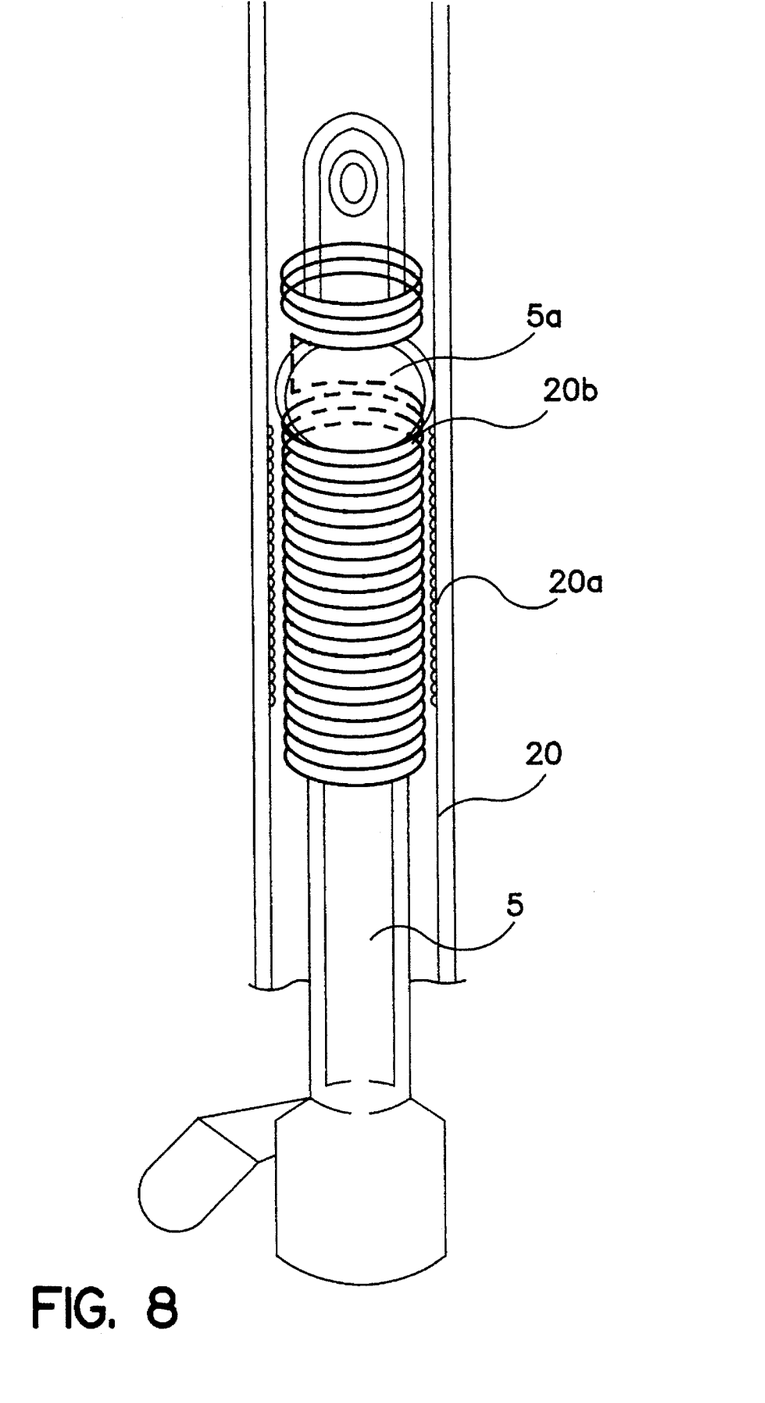
FIG. 8 is an explanatory diagram showing an accurate positioning of an SMA stent for a biliary tract or a blood vessel by inflating a bag.

First a 0.35 mm flexible tipped guide wipe is inserted into a narrow segment 20a of the biliary tract or the blood vessel 20. Then the catheter which carries the SMA stent is passed over the guide wire so that the proximal portion 1 and the interspace portion 3 of the stent pass through a stricture 20a. Then in the same way as the above for the urethra stent, water is infused into the catheter, causing the bag portion 5a of the catheter to be bulged. Then, the catheter 5 with the stent is pulled outwardly until it abuts against the narrowing interior end wall 20b of the narrow segment 20a, as shown in FIG. 8. This positions the stent accurately in the desired position.

After this positioning state, the catheter 5 is deflated. Next, saline at a temperature of from 41° C. to 43° C. is infused through the catheter to heat it up approximately the same temperature. This causes the stent to expand and loosen from the catheter 5, and furthermore to be detained in contact with the entire wall of mucosa. Pulling the catheter 5 from the stent leaves the stent in the right position in the biliary tract of the blood vessel.

Removal of the SMA stent may be achieved by the same manner as the urethral stent. It is preferable that the stent has a floppy stainless tip at the end of the distal portion 2 so that the stent may be retrieved with a strong magnet device.

SMA stent, for a biliary, urethral and vascular system according to the present invention have the following advantages.

When a stent is inserted into the system, it is in the configuration of a contracted cylinder. This facilitates the insertion procedure and allows the stent to expand to the desired shape at the Af temperature phase. The stent may be expanded in a simple manner by infusing saline at the Af temperature. The configuration at and above the Af temperature is an expanded combination of a funnel portion and a cylindrical portion, so that the funnel portion may contact with the narrowing interior end wall of the narrow segment and the stent stays in the right position firmly. By cooling with cold saline, the stent is super-elastically transform into a fine cylinder shape or a straightened wire, thereby allowing easy removal.

The stent of the present invention is more suitable for hemostatics after the bleeding relating to surgical intervention than any other maneuvers such as traction with indwelled balloon catheter, since the expansion of the SMA stent allows the stent to compress directly towards the prostatic bed or the like. Indirect visceral wall compression through excessive traction at the area of bleeding inevitably causes adverse reactions.

What is claimed is:

1. A stent for a biliary, urinary or vascular system, the stent being made of a shape memory alloy having an Austenite finished temperature ranging from 41° to 43° C. and having a first configuration at a temperature below the Austenite finished temperature and a second expanded configuration at or above the Austenite finished temperature and wherein in the first configuration, a proximal cylindrical portion (1), a distal cylindrical portion (2) and an interspace (3) connecting the two portions (1 ,2) therebetween, through which a portion of a catheter is bulged out to facilitate positioning of the stent in the system, and in the second configuration, the distal portion (2) expands in diameter, the proximal portion (1) is flared away from the expanded distal portion (2), and the interspace (3) is reduced to be absorbed into a shape directly combining the portions (1, 2) so that the stent becomes funnel-shaped to be reliably anchored by the flared proximal portion (1) after the positioning.

2. A stent according to claim 1 wherein the proximal portion (1) and the distal portion (2) are both in a coiled shape.

3. A stent according to claim 1 wherein the proximal portion (1) and the distal portion (2) are made of mesh.

4. A stent according to claim 1 wherein in the first configuration the cross section of the cylindrical portion (1, 2) is ellipsoidal or circular.

5. A stent according to claim 1, wherein in the first configuration the length of the distal portion (2) is longer than that of the proximal portion (1).

6. A stent according to claim 1 wherein in the first configuration the cross section of the cylindrical portion is circular.

7. A stent according to claim 1, wherein in the first configuration the interspace (3) includes a straight wire portion (4) by which the proximal cylindrical portion (1) and the distal cylindrical portion (2) are connected together.

8. A method of locating a stent in a desired position in a biliary, urinary or vascular system, the method comprising:

mounting a stent on an inflatable catheter, said stent being made of a shape memory alloy having an Austenite finished temperature ranging from 41° C. to 43° C. and having a first configuration at a temperature below the Austenite finished temperature and a second expanded configuration at or above the Austenite finished temperature, said stent further having in the first configuration a proximal portion, a distal portion and an interspace therebetween;

inserting the catheter carrying the stent into the system;

inflating the catheter at least at or near the interspace of the stent so that a portion of the inflated catheter is bulged out through the interspace to facilitate accurate positioning of the stent; and raising the temperature of the stent so that the stent assumes its second expanded funnel-shaped configuration to be reliably retained after the positioning.

9. A method according to claim 8 wherein the catheter carrying the stent is inserted into the system in a way that the proximal portion and the interspace of the stent are passed over a narrow segment, and the inflated catheter is accurately positioned by being pulled outwardly until the inflated portion thereof comes to abut against the narrow segment.

* * * * *